(12) United States Patent
de Baeremaecker Barros

(10) Patent No.: US 10,213,500 B2
(45) Date of Patent: Feb. 26, 2019

(54) MULTICOMPONENT OR MONOCOMPONENT VACCINE TO BE USED AGAINST CHAGAS DISEASE, PHARMACEUTICAL COMPOSITIONS CONTAINING THEM, PROCEDURE FOR THE OBTENTION OF IMMUNOGEN OF SAID VACCINES, AND NUCLEIC ACID USED IN SAID PROCEDURE

(71) Applicant: Carlos de Baeremaecker Barros, Montevideo (UY)

(72) Inventor: Carlos de Baeremaecker Barros, Montevideo (UY)

( * ) Notice: Subject to any disclaimer, the term of this patent is extended or adjusted under 35 U.S.C. 154(b) by 0 days.

(21) Appl. No.: 15/492,365

(22) Filed: Apr. 20, 2017

(65) Prior Publication Data

US 2017/0290896 A1    Oct. 12, 2017

Related U.S. Application Data

(62) Division of application No. 14/529,454, filed on Oct. 31, 2014, now Pat. No. 9,662,378, which is a division of application No. 12/740,393, filed as application No. PCT/IB2008/002923 on Oct. 30, 2008, now Pat. No. 8,900,598.

(30) Foreign Application Priority Data

Oct. 31, 2007 (AR) ............................. P20070104827

(51) Int. Cl.
*A61K 39/005* (2006.01)
*A61K 39/002* (2006.01)
*A61K 39/00* (2006.01)

(52) U.S. Cl.
CPC .......... *A61K 39/005* (2013.01); *A61K 39/002* (2013.01); *A61K 39/00* (2013.01); *A61K 2039/53* (2013.01); *A61K 2039/55505* (2013.01); *A61K 2039/55522* (2013.01); *A61K 2039/55527* (2013.01); *Y02A 50/414* (2018.01)

(58) Field of Classification Search
None
See application file for complete search history.

(56) References Cited

U.S. PATENT DOCUMENTS 8,900,598 B2 *  12/2014  de Baeremaecker Barros ............ A61K 39/005 424/269.1
9,662,378 B2 *  5/2017   de Baeremaecker Barros ............ A61K 39/005

* cited by examiner

*Primary Examiner* — Jennifer E Graser
(74) *Attorney, Agent, or Firm* — Patent Central LLC; Stephan A. Pendorf

(57) ABSTRACT

A monocomponent vaccine effective to moderate the clinical consequences of Chages disease, capable of stimulating an immune response against the trans-sialidase virulence factor of the *Trypanosoma cruzi* parasite. The vaccine active ingredient is an immunogenic component with a polynucleotide encoding one or more polypeptide(s) which includes a C-terminal region composed of at least two repetitive units of amino acids, with a polypeptide with trans-sialidase activity of *Trypanosoma cruzi* fused to the C-terminal region. The vaccine further comprises an aluminum oxide adjuvant that does not inhibit trans-sialidase enzymatic activity of the immunogen portion.

19 Claims, 4 Drawing Sheets

Specification includes a Sequence Listing.

```
        |   10       |   20       |   30       |   40       |   50       |   60
   10              a tgCTGGCACC CGGATCGAGC CGAGTTGAGC TGTTTAAGCG GCAAAGCTCG  60
   61 AAGGTGCCAT TTGAAAAGGA CGGCAAAGTC ACCGAGCGGG TTGTCCACTC GTTCCGCCTC 120
  121 CCCGCCCTTG TTAATGTGGA CGGGGTGATG GTTGCCATCG CGGACGCTCG CTACGAAACA 180
  181 TCCAATGACA ACTCCCTCAT TGATACGGTG GCGAAGTACA GCGTGGACGA TGGGGAGACG 240
  241 TGGGAGACCC AAATTGCCAT CAAGAACAGT CGTGCATCGT CTGTTTCTCG TGTGGTGGAT 300
  301 CCCACAGTGA TTGTGAAGGG CAACAAGCTT TACGTCCTGG TTGGAAGCTA CAACAGTTCG 360
  361 AGGAGCTACT GGACGTCGCA TGGTGATGCG AGAGACTGGG ATATTCTGCT TGCCGTTGGT 420
  421 GAGGTCACGA AGTCCACTGC GGGCGGCAAG ATAACTGCGA GTATCAAATG GGGGAGCCCC 480
  481 GTGTCACTGA AGGAATTTTT TCCGGCGAAA ATGGAAGGAA TGCACACAAA TCAATTTCTT 540
  541 GGCGGTGCAG GTGTTGCCAT TGTGGCGTCC AACGGGAATC TTGTGTACCC TGTGCAGGTT 600
  601 ACGAACAAAA AGAAGCAAGT TTTTTCCAAG ATCTTCTACT CGGAAGACGA GGGCAAGACG 660
  661 TGGAAGTTTG GGAAGGGTAG GAGCGCTTTT GGCTGCTCTG AACCTGTGGC CCTTGAGTGG 720
  721 GAGGGGAAGC TCATCATAAA CACTCGAGTT GACTATCGCC GCCGTCTGGT GTACGAGTCC 780
  781 AGTGACATGG GGAATTCGTG GCTGGAGGCT GTCGGCACGC TCTCACGTGT GTGGGGCCCC 840
  841 TCACCAAAAT CGAACCAGCC CGGCAGTCAG AGCAGCTTCA CTGCCGTGAC CATCGAGGGA 900
  901 ATGCGTGTTA TGCTCTTCAC ACACCCGCTG AATTTTAAGG GAAGGTGGCT GCGCGACCGA 960
  961 CTGAACCTCT GGCTGACGGA TAACCAGCGC ATTTATAACG TTGGGCAAGT ATCCATTGGT 1020
 1021 GATGAAAATT CCGCCTACAG CTCCGTCCTG TACAAGGATG ATAAGCTGTA CTGTTTGCAT 1080
 1081 GAGATCAACA GTAACGAGGT GTACAGCCTT GTTTTTGCGC GCCTGGTTGG CGAGCTACGG 1140
 1141 ATCATTAAAT CAGTGCTGCA GTCCTGGAAG AATTGGGACA GCCACCTGTC CAGCATTTGC 1200
 1201 ACCCCTGCTG ATCCAGCCGC TTCGTCGTCA GAGCGTGGTT GTGGTCCCGC TGTCACCACG 1260
 1261 GTTGGTCTTG TTGGCTTTTT GTCGCACAGT GCCACCAAAA CCGAATGGGA GGATGCGTAC 1320
 1321 CGCTGCGTGA ACGCAAGCAC GGCAAATGCG GAGAGGGTTC CGAACGGTTT GAAGTTTGCG 1380
 1381 GGGGTTGGCG GAGGGCGCT TTGGCCGGTG AGCCAGCAGG GGCAGAATCA ACGGTATCGC 1440
 1441 TTTGCAAACC ACGCGTTCAC CGTGGTGGCG TCGGTGACGA TTCACGAGGT TCCGAGCGTC 1500
 1501 GCGAGTCCTT TGCTGGGTGC GAGCCTGGAC TCTTCTGGTG GCAAAAAACT CCTGGGGCTC 1560
 1561 TCGTACACG AGAGGCACCA GTGGCAGCCA ATATACGGAT CAACGCCGGT GACGCCGACC 1620
 1621 GGATCGTGGG AGATGGGTAA GAGGTACCAC GTGGTTCTTA CGATGGCGAA TAAAATTGGC 1680
 1681 TCCGAGTACA TTGATGGAGA ACCTCTGGAG GGTTCAGGGC AGACCGTTGT GCCAGACGAG 1740
 1741 AGGACGCCTG ACATCTCCCA CTTCTACGTT GGCGGGTATA AAAGGAGTGA TATGCCAACC 1800
 1801 ATAAGCCACG TGACGGTGAA TAATGTTCTT CTTTACAACC GTCAGCTGAA TGCCGAGGAG 1860
 1861 ATCAGGACCT TGTTCTTGAG..CCAGGACCTG ATTGGCACGG AAGCACACAT GGACAGCAGC 1920
 1921 AGCGACACGA GTGCCtga                                               1938
        |   10       |   20       |   30       |   40       |   50       |   60
```

FIG. 1

```
        |   10       |   20       |   30       |   40       |   50       |   60
    5            LAPGSS RVELFKRQSS KVPFEKDGKV TERVVHSFRL PALVNVDGVM VAIADARYET  60
   61 SNDNSLIDTV AKYSVDDGET WETQIAIKNS RASSVSRVVD PTVIVKGNKL YVLVGSYNSS 120
  121 RSYWTSHGDA RDWDILLAVG EVTKSTAGGK ITASIKWGSP VSLKEFFPAE MEGMHTNQFL 180
  181 GGAGVAIVAS NGNLVYPVQV TNKKQVFSK IFYSEDEGKT WKFGKGRSAF GCSEPVALEW 240
  241 EGKLIINTRV DYRRRLVYES SDMGNSWLEA VGTLSRVWGP SPKSNQPGSQ SSFTAVTIEG 300
  301 MRVMLFTHPL NFKGRWLRDR LNLWLTDNQR IYNVGQVSIG DENSAYSSVL YKDDKLYCLH 360
  361 EINSNEVYSL VFARLVGELR IIKSVLQSWK NWDSHLSSIC TPADPAASSS ERGCGPAVTT 420
  421 VGLVGFLSHS ATKTEWEDAY RCVNASTANA ERVPNGLKFA GVGGGALWPV SQQGQNQRYR 480
  481 FANHAFTVVA SVTIHEVPSV ASPLLGASLD SSGGKKLLGL SYDERHQWQP IYGSTPVTPT 540
  541 GSWEMGKRYH VVLTMANKIG SEYIDGEPLE GSGQTVVPDE RTPDISHFYV GGYKRSDMPT 600
  601 ISHVTVNNVL LYNRQLNAEE IRTLFLSQDL IGTEAHMDSS SDTSAZ                649
        |   10       |   20       |   30       |   40       |   50       |   60
```

FIG. 2

```
              |  10       |  20       |  30       |  40       |  50       |  60
3037                                             AGTG  CCCACGGTAC GCCCTCAACT 3060
3061 CCCGTTGACA GCACTGCCCA CGGTACGCCC TCGACTCCCG CTGACAGCAG TGCCCACAGT 3120
3121 ACGCCCTCGA CTCCCGCTGA CAGCAGTGCC CACAGTACGC CCTCGACTCC CGTTGACAGC 3180
3181 AGTGCCCACA GTACGCCCTC GACTCCCGCT GACAGCAGTG CCCACAGTAC GCCCTCGACT 3240
3241 CCCGCTGACA GCAGTGCCCA CAGTACGCCC TCAACTCCCG TTGACAGCAC TGCCCACGGT 3300
3301 ACGCCCTCGA CTCCCGCTGA CAGCAGTGCC CACAGTACGC CCTCAACTCC CGTTGACAGC 3360
3361 AGTGCCCACA GTACGCCCTC GACTCCCGCT GACAGCAGTG CCCACAGTAC GCCCTCAACT 3420
3421 CCCGTTGACA GCAGTGCCCA CAGTACGCCC TCGACTCCCG CTGACAGCAG TGCCCACGGT 3480
3481 ACGCCCTCGA CTCCCGTTGA CAGCAGTGCC CACAGTACGC CCTCAACTCC CGCTGACAGC 3540
3541 AGTGCCAATG GTACGGTTTT GATTTTGCCC GATGGCGCTG CACTTTCCAC CTTTTCGGGC 3600
3601 GGAGGGCTTC TTCTGTGTGC GTGTGCTTTG CTGCTGCACG TGTTTTTTAC GGCAGTTTTT 3660
3661 TTCTGAtgt                                                              3669
              |  10       |  20       |  30       |  40       |  50       |  60
```

FIG. 3

```
              |  10       |  20       |  30       |  40       |  50       |  60
  1 SAHGTPSTPV DSTAHGTPST PADSSAHSTP STPADSSAHS TPSTPVDSSA HSTPSTPADS  60
 61 SAHSTPSTPA DSSAHSTPST PVDSTAHGTP STPADSSAHS TPSTPVDSSA HSTPSTPADS 120
121 SAHSTPSTPV DSSAHSTPST PADSSAHGTP STPVDSSAHS TPSTPADSSA NGTVLILPDG 180
181 AALSTFSGGG LLLCACALLL HVFFTAVFFZ                                  211
              |  10       |  20       |  30       |  40       |  50       |  60
```

FIG. 4

```
1/1                                            31/11
atg CTG GCA CCC GGA TCG AGC CGA GTT GAG CTG TTT AAG CGG CAA AGC TCG AAG GTG CCA
 M   L   A   P   G   S   S   R   V   E   L   F   K   R   Q   S   S   K   V   P
61/21                                          91/31
TTT GAA AAG GAC GGC AAA GTC ACC GAG CGG GTT GTC CAC TCG TTC CGC CTC CCC GCC CTT
 F   E   K   D   G   K   V   T   E   R   V   V   H   S   F   R   L   P   A   L
121/41                                         151/51
GTT AAT GTG GAC GGG GTG ATG GTT GCC ATC GCG GAC GCT CGC TAC GAA ACA TCC AAT GAC
 V   N   V   D   G   V   M   V   A   I   D   A   R   Y   E   T   S   N   D
181/61                                         211/71
AAC TCC CTC ATT GAT ACG GTG GCG AAG TAC AGC GTG GAC GAT GGG GAG ACG TGG GAG ACC
 N   S   L   I   D   T   V   A   K   Y   S   V   D   D   G   E   T   W   E   T
241/81                                         271/91
CAA ATT GCC ATC AAG AAC AGT CGT GCA TCG TCT GTT TCT CGT GTG GTG GAT CCC ACA GTG
 Q   I   A   I   K   N   S   R   A   S   S   V   S   R   V   V   D   P   T   V
301/101                                        331/111
ATT GTG AAG GGC AAC AAG CTT TAC GTC CTG GTT GGA AGC TAC AAC AGT TCG AGG AGC TAC
 I   V   K   G   N   K   L   Y   V   L   V   G   S   Y   N   S   S   R   S   Y
361/121                                        391/131
TGG ACG TCG CAT GGT GAT GCG AGA GAC TGG GAT ATT CTG CTT GCC GTT GGT GAG GTC ACG
 W   T   S   H   G   D   A   R   D   W   D   I   L   L   A   V   G   E   V   T
421/141                                        451/151
AAG TCC ACT GCG GGC GGC AAG ATA ACT GCG AGT ATC AAA TGG GGG AGC CCC GTG TCA CTG
 K   S   T   A   G   G   K   I   T   A   S   I   K   W   G   S   P   V   S   L
481/161                                        511/171
AAG GAA TTT TTT CCG GCG GAA ATG GAA GGA ATG CAC ACA AAT CAA TTT CTT GGC GGT GCA
 K   E   F   F   P   A   E   M   E   G   M   H   T   N   Q   F   L   G   G   A
541/181                                        571/191
GGT GTT GCC ATT GTG GCG TCC AAC GGG AAT CTT GTG TAC CCT GTG CAG GTT ACG AAC AAA
 G   V   A   I   V   A   S   N   G   N   L   V   Y   P   V   Q   V   T   N   K
601/201                                        631/211
AAG AAG CAA GTT TTT TCC AAG ATC TTC TAC TCG GAA GAC GAG GGC AAG ACG TGG AAG TTT
 K   K   Q   V   F   S   K   I   F   Y   S   E   D   E   G   K   T   W   K   F
661/221                                        691/231
GGG AAG GGT AGG AGC GCT TTT GGC TGC TCT GAA CCT GTG GCC CTT GAG TGG GAG GGG AAG
 G   K   G   R   S   A   F   G   C   S   E   P   V   A   L   E   W   E   G   K
721/241                                        751/251
CTC ATC ATA AAC ACT CGA GTT GAC TAT CGC CGC CGT CTG GTG TAC GAG TCC AGT GAC ATG
 L   I   I   N   T   R   V   D   Y   R   R   R   L   V   Y   E   S   S   D   M
781/261                                        811/271
GGG AAT TCG TGG CTG GAG GCT GTC GGC ACG CTC TCA CGT GTG TGG GGC CCC TCA CCA AAA
 G   N   S   W   L   E   A   V   G   T   L   S   R   V   W   G   P   S   P   K
841/281                                        871/291
TCG AAC CAG CCC GGC AGT CAG AGC AGC TTC ACT GCC GTG ACC ATC GAG GGA ATG CGT GTT
 S   N   Q   P   G   S   Q   S   S   F   T   A   V   T   I   E   G   M   R   V
901/301                                        931/311
ATG CTC TTC ACA CAC CCG CTG AAT TTT AAG GGA AGG TGG CTG CGC GAC CGA CTG AAC CTC
 M   L   F   T   H   P   L   N   F   K   G   R   W   L   R   D   R   L   N   L
961/321                                        991/331
TGG CTG ACG GAT AAC CAG CGC ATT TAT AAC GTT GGG CAA GTA TCC ATT GGT GAT GAA AAT
 W   L   T   D   N   Q   R   I   Y   N   V   G   Q   V   S   I   G   D   E   N
1021/341                                       1051/351
TCC GCC TAC AGC TCC GTC CTG TAC AAG GAT GAT AAG CTG TAC TGT TTG CAT GAG ATC AAC
 S   A   Y   S   S   V   L   Y   K   D   D   K   L   Y   C   L   H   E   I   N
1081/361                                       1111/371
AGT AAC GAG GTG TAC AGC CTT GTT TTT GCG CGC CTG GTT GGC GAG CTA CGG ATC ATT AAA
 S   N   E   V   Y   S   L   V   F   A   R   L   V   G   E   L   R   I   I   K
1141/381                                       1171/391
TCA GTG CTG CAG TCC TGG AAG AAT TGG GAC AGC CAC CTG TCC AGC ATT TGC ACC CCT GCT
 S   V   L   Q   S   W   K   N   W   D   S   H   L   S   S   I   C   T   P   A
1201/401                                       1231/411
GAT CCA GCC GCT TCG TCG TCA GAG CGT GGT TGT GGT CCC GCT GTC ACC ACG GTT GGT CTT
 D   P   A   A   S   S   S   E   R   G   C   G   P   A   V   T   T   V   G   L
```

FIG. 5

```
1261/421                                    1291/431
GTT GGC TTT TTG TCG CAC AGT GCC ACC AAA ACC GAA TGG GAG GAT GCG TAC CGC TGC GTG
 V   G   F   L   S   H   S   A   T   K   T   E   W   E   D   A   Y   R   C   V
1321/441                                    1351/451
AAC GCA AGC ACG GCA AAT GCG GAG AGG GTT CCG AAC GGT TTG AAG TTT GCG GGG GTT GGC
 N   A   S   T   A   N   A   E   R   V   P   N   G   L   K   F   A   G   V   G
1381/461                                    1411/471
GGA GGG GCG CTT TGG CCG GTG AGC CAG CAG GGG CAG AAT CAA CGG TAT CGC TTT GCA AAC
 G   G   A   L   W   P   V   S   Q   Q   G   Q   N   Q   R   Y   R   F   A   N
1441/481                                    1471/491
CAC GCG TTC ACC GTG GTG GCG TCG GTG ACG ATT CAC GAG GTT CCG AGC GTC GCG AGT CCT
 H   A   F   T   V   V   A   S   V   T   I   H   E   V   P   S   V   A   S   P
1501/501                                    1531/511
TTG CTG GGT GCG AGC CTG GAC TCT TCT GGT GGC AAA AAA CTC CTG GGG CTC TCG TAC GAC
 L   L   G   A   S   L   D   S   S   G   G   K   K   L   L   G   L   S   Y   D
1561/521                                    1591/531
GAG AGG CAC CAG TGG CAG CCA ATA TAC GGA TCA ACG CCG GTG ACG CCG ACC GGA TCG TGG
 E   R   H   Q   W   Q   P   I   Y   G   S   T   P   V   T   P   T   G   S   W
1621/541                                    1651/551
GAG ATG GGT AAG AGG TAC CAC GTG GTT CTT ACG ATG GCG AAT AAA ATT GGC TCC GAG TAC
 E   M   G   K   R   Y   H   V   V   L   T   M   A   N   K   I   G   S   E   Y
1681/561                                    1711/571
ATT GAT GGA GAA CCT CTG GAG GGT TCA GGG CAG ACC GTT GTG CCA GAC GAG AGG ACG CCT
 I   D   G   E   P   L   E   G   S   G   Q   T   V   V   P   D   E   R   T   P
1741/581                                    1771/591
GAC ATC TCC CAC TTC TAC GTT GGC GGG TAT AAA AGG AGT GAT ATG CCA ACC ATA AGC CAC
 D   I   S   H   F   Y   V   G   G   Y   K   R   S   D   M   P   T   I   S   H
1801/601                                    1831/611
GTG ACG GTG AAT AAT GTT CTT CTT TAC AAC CGT CAG CTG AAT GCC GAG GAG ATC AGG ACC
 V   T   V   N   N   V   L   L   Y   N   R   Q   L   N   A   E   E   I   R   T
1861/621                                    1891/631
TTG TTC TTG AGC CAG GAC CTG ATT GGC ACG GAA GCA CAC ATG GAC AGC AGC AGC GAC ACG
 L   F   L   S   Q   D   L   I   G   T   E   A   H   M   D   S   S   S   D   T
1921/641                                    1951/651
AGT GCC AGT GCC CAC GGT ACG CCC TCA ACT CCC GTT GAC AGC ACT GCC CAC GGT ACG CCC
 S   A   S   A   H   G   T   P   S   T   P   V   D   S   T   A   H   G   T   P
1981/661                                    2011/671
TCG ACT CCC GCT GAC AGC AGT GCC CAC AGT ACG CCC TCG ACT CCC GCT GAC AGC AGT GCC
 S   T   P   A   D   S   S   A   H   S   T   P   S   T   P   A   D   S   S   A
2041/681                                    2071/691
CAC AGT ACG CCC TCG ACT CCC GTT GAC AGC AGT GCC CAC AGT ACG CCC TCG ACT CCC GCT
 H   S   T   P   S   T   P   V   D   S   S   A   H   S   T   P   S   T   P   A
2101/701                                    2131/711
GAC AGC AGT GCC CAC AGT ACG CCC TCG ACT CCC GCT GAC AGC AGT GCC CAC AGT ACG CCC
 D   S   S   A   H   S   T   P   S   T   P   A   D   S   S   A   H   S   T   P
2161/721                                    2191/731
TCA ACT CCC GTT GAC AGC ACT GCC CAC GGT ACG CCC TCG ACT CCC GCT GAC AGC AGT GCC
 S   T   P   V   D   S   T   A   H   G   T   P   S   T   P   A   D   S   S   A
2221/741                                    2251/751
CAC AGT ACG CCC TCA ACT CCC GTT GAC AGC AGT GCC CAC AGT ACG CCC TCG ACT CCC GCT
 H   S   T   P   S   T   P   V   D   S   S   A   H   S   T   P   S   T   P   A
2281/761                                    2311/771
GAC AGC AGT GCC CAC AGT ACG CCC TCA ACT CCC GTT GAC AGC AGT GCC CAC AGT ACG CCC
 D   S   S   A   H   S   T   P   S   T   P   V   D   S   S   A   H   S   T   P
2341/781                                    2371/791
TCG ACT CCC GCT GAC AGC AGT GCC CAC GGT ACG CCC TCG ACT CCC GTT GAC AGC AGT GCC
 S   T   P   A   D   S   S   A   H   G   T   P   S   T   P   V   D   S   S   A
2401/801                                    2431/811
CAC AGT ACG CCC TCA ACT CCC GCT GAC AGC AGT GCC AAT GGT ACG GTT TTG ATT TTG CCC
 H   S   T   P   S   T   P   A   D   S   S   A   N   G   T   V   L   I   L   P
2461/821                                    2491/831
GAT GGC GCT GCA CTT TCC ACC TTT TCG GGC GGA GGG CTT CTT CTG TGT GCG TGT GCT TTG
 D   G   A   A   L   S   T   F   S   G   G   G   L   L   L   C   A   C   A   L
2521/841                                    2551/851
CTG CTG CAC GTG TTT TTT ACG GCA GTT TTT TTC TGA
 L   L   H   V   F   F   T   A   V   F   F   *
```

FIG. 5, continued

SEQUENCE LISTING

<160> NUMBER OF SEQ ID NOS: 7

<210> SEQ ID NO 1
<211> LENGTH: 1929
<212> TYPE: DNA
<213> ORGANISM: Trypanosoma cruzi

<400> SEQUENCE: 1

```
atgctggcac ccggatcgag ccgagttgag ctgtttaagc ggcaaagctc gaaggtgcca      60
tttgaaaagg acggcaaagt caccgagcgg gttgtccact cgttccgcct ccccgccctt     120
gttaatgtgg acggggtgat ggttgccatc gcggacgctc gctacgaaac atccaatgac     180
aactccctca ttgatacggt ggcgaagtac agcgtggacg atggggagac gtgggagacc     240
caaattgcca tcaagaacag tcgtgcatcg tctgtttctc gtgtggtgga tcccacagtg     300
attgtgaagg gcaacaagct ttacgtcctg gttggaagct acaacagttc gaggagctac     360
tggacgtcgc atggtgatgc gagagactgg gatattctgc ttgccgttgg tgaggtcacg     420
aagtccactg cgggcggcaa gataactgcg agtatcaaat ggggagcccc cgtgtcactg     480
aaggaatttt ttccggcgga aatggaagga atgcacacaa atcaatttct tggcggtgca     540
ggtgttgcca ttgtggcgtc caacgggaat cttgtgtacc ctgtgcaggt tacgaacaaa     600
aagaagcaag ttttttccaa gatcttctac tcggaagacg agggcaagac gtggaagttt     660
gggaagggta ggagcgcttt tggctgctct gaacctgtgg cccttgagtg ggaggggaag     720
ctcatcataa acactcgagt tgactatcgc cgccgtctgg tgtacgagtc cagtgacatg     780
gggaattcgt ggctggaggc tgtcggcacg ctctcacgtg tgtggggccc ctcaccaaaa     840
tcgaaccagc ccggcagtca gagcagcttc actgccgtga ccatcgaggg aatgcgtgtt     900
atgctcttca cacacccgct gaattttaag ggaaggtggc tgcgcgaccg actgaacctc     960
tggctgacgg ataaccagcg catttataac gttgggcaag tatccattgg tgatgaaaat    1020
tccgcctaca gctccgtcct gtacaaggat gataagctgt actgtttgca tgagatcaac    1080
agtaacgagg tgtacagcct tgtttttgcg cgcctggttg gcgagctacg gatcattaaa    1140
tcagtgctgc agtcctggaa gaattgggac agccacctgt ccagcatttg caccccctgct   1200 gatccagccg cttcgtcgtc agagcgtggt tgtggtcccg ctgtcaccac ggttggtctt    1260 gttggcttt tgtcgcacag tgccaccaaa accgaatggg aggatgcgta ccgctgcgtg     1320
aacgcaagca cggcaaatgc ggagagggtt ccgaacggtt tgaagtttgc ggggttggc     1380 ggaggggcgc tttggccggt gagccagcag gggcagaatc aacggtatcg ctttgcaaac    1440
cacgcgttca ccgtggtggc gtcggtgacg attcacgagg ttccgagcgt cgcgagtcct    1500
ttgctgggtg cgagcctgga ctcttctggt ggcaaaaaac tcctggggct ctcgtacgac    1560
gagaggcacc agtggcagcc aatatacgga tcaacgccgg tgacgccgac cggatcgtgg    1620
gagatgggta agaggtacca cgtggttctt acgatggcga ataaaattgg ctccgagtac    1680
```

-continued

```
attgatggag aacctctgga gggttcaggg cagaccgttg tgccagacga gaggacgcct    1740
gacatctccc acttctacgt tggcgggtat aaaaggagtg atatgccaac cataagccac    1800
gtgacggtga ataatgttct tctttacaac cgtcagctga atgccgagga gatcaggacc    1860
ttgttcttga gccaggacct gattggcacg gaagcacaca tggacagcag cagcgacacg    1920
agtgcctga                                                            1929
```

<210> SEQ ID NO 2
<211> LENGTH: 641
<212> TYPE: PRT
<213> ORGANISM: Trypanosoma cruzi

<400> SEQUENCE: 2

```
Leu Ala Pro Gly Ser Ser Arg Val Glu Leu Phe Lys Arg Gln Ser Ser
1               5                   10                  15

Lys Val Pro Phe Glu Lys Asp Gly Lys Val Thr Glu Arg Val Val His
            20                  25                  30

Ser Phe Arg Leu Pro Ala Leu Val Asn Val Asp Gly Val Met Val Ala
        35                  40                  45

Ile Ala Asp Ala Arg Tyr Glu Thr Ser Asn Asp Asn Ser Leu Ile Asp
    50                  55                  60

Thr Val Ala Lys Tyr Ser Val Asp Asp Gly Glu Thr Trp Glu Thr Gln
65                  70                  75                  80

Ile Ala Ile Lys Asn Ser Arg Ala Ser Ser Val Ser Arg Val Val Asp
                85                  90                  95

Pro Thr Val Ile Val Lys Gly Asn Lys Leu Tyr Val Leu Val Gly Ser
            100                 105                 110

Tyr Asn Ser Ser Arg Ser Tyr Trp Thr Ser His Gly Asp Ala Arg Asp
        115                 120                 125

Trp Asp Ile Leu Leu Ala Val Gly Glu Val Thr Lys Ser Thr Ala Gly
    130                 135                 140

Gly Lys Ile Thr Ala Ser Ile Lys Trp Gly Ser Pro Val Ser Leu Lys
145                 150                 155                 160

Glu Phe Phe Pro Ala Glu Met Glu Gly Met His Thr Asn Gln Phe Leu
                165                 170                 175

Gly Gly Ala Gly Val Ala Ile Val Ala Ser Asn Gly Asn Leu Val Tyr
            180                 185                 190

Pro Val Gln Val Thr Asn Lys Lys Gln Val Phe Ser Lys Ile Phe
        195                 200                 205

Tyr Ser Glu Asp Glu Gly Lys Thr Trp Lys Phe Gly Lys Gly Arg Ser
    210                 215                 220

Ala Phe Gly Cys Ser Glu Pro Val Ala Leu Glu Trp Glu Gly Lys Leu
225                 230                 235                 240

Ile Ile Asn Thr Arg Val Asp Tyr Arg Arg Leu Val Tyr Glu Ser
                245                 250                 255

Ser Asp Met Gly Asn Ser Trp Leu Glu Ala Val Gly Thr Leu Ser Arg
            260                 265                 270

Val Trp Gly Pro Ser Pro Lys Ser Asn Gln Pro Gly Ser Gln Ser Ser
        275                 280                 285

Phe Thr Ala Val Thr Ile Glu Gly Met Arg Val Met Leu Phe Thr His
    290                 295                 300

Pro Leu Asn Phe Lys Gly Arg Trp Leu Arg Asp Arg Leu Asn Leu Trp
305                 310                 315                 320

Leu Thr Asp Asn Gln Arg Ile Tyr Asn Val Gly Gln Val Ser Ile Gly
```

325                 330                 335
Asp Glu Asn Ser Ala Tyr Ser Ser Val Leu Tyr Lys Asp Asp Lys Leu
                340                 345                 350
Tyr Cys Leu His Glu Ile Asn Ser Asn Glu Val Tyr Ser Leu Val Phe
            355                 360                 365
Ala Arg Leu Val Gly Glu Leu Arg Ile Ile Lys Ser Val Leu Gln Ser
        370                 375                 380
Trp Lys Asn Trp Asp Ser His Leu Ser Ser Ile Cys Thr Pro Ala Asp
385                 390                 395                 400
Pro Ala Ala Ser Ser Glu Arg Gly Cys Gly Pro Ala Val Thr Thr
                405                 410                 415
Val Gly Leu Val Gly Phe Leu Ser His Ser Ala Thr Lys Thr Glu Trp
                420                 425                 430
Glu Asp Ala Tyr Arg Cys Val Asn Ala Ser Thr Ala Asn Ala Glu Arg
                435                 440                 445
Val Pro Asn Gly Leu Lys Phe Ala Gly Val Gly Gly Ala Leu Trp
                450                 455                 460
Pro Val Ser Gln Gln Gly Gln Asn Gln Arg Tyr Arg Phe Ala Asn His
465                 470                 475                 480
Ala Phe Thr Val Val Ala Ser Val Thr Ile His Glu Val Pro Ser Val
                485                 490                 495
Ala Ser Pro Leu Leu Gly Ala Ser Leu Asp Ser Ser Gly Gly Lys Lys
                500                 505                 510
Leu Leu Gly Leu Ser Tyr Asp Glu Arg His Gln Trp Gln Pro Ile Tyr
            515                 520                 525
Gly Ser Thr Pro Val Thr Pro Thr Gly Ser Trp Glu Met Gly Lys Arg
        530                 535                 540
Tyr His Val Val Leu Thr Met Ala Asn Lys Ile Gly Ser Glu Tyr Ile
545                 550                 555                 560
Asp Gly Glu Pro Leu Glu Gly Ser Gly Gln Thr Val Val Pro Asp Glu
                565                 570                 575
Arg Thr Pro Asp Ile Ser His Phe Tyr Val Gly Gly Tyr Lys Arg Ser
                580                 585                 590
Asp Met Pro Thr Ile Ser His Val Thr Val Asn Asn Val Leu Leu Tyr
                595                 600                 605
Asn Arg Gln Leu Asn Ala Glu Glu Ile Arg Thr Leu Phe Leu Ser Gln
            610                 615                 620
Asp Leu Ile Gly Thr Glu Ala His Met Asp Ser Ser Ser Asp Thr Ser
625                 630                 635                 640
Ala

<210> SEQ ID NO 3
<211> LENGTH: 633
<212> TYPE: DNA
<213> ORGANISM: Trypanosoma cruzi

<400> SEQUENCE: 3
agtgcccacg gtacgccctc aactcccgtt gacagcactg cccacggtac gccctcgact      60
cccgctgaca gcagtgccca cagtacgccc tcgactcccg ctgacagcag tgcccacagt     120
acgccctcga ctcccgttga cagcagtgcc cacagtacgc cctcgactcc cgctgacagc     180
agtgcccaca gtacgccctc gactcccgct gacagcagtg cccacagtac gccctcaact     240
cccgttgaca gcactgccca cggtacgccc tcgactcccg ctgacagcag tgcccacagt     300

-continued

| | |
|---|---|
| acgccctcaa ctcccgttga cagcagtgcc cacagtacgc cctcgactcc cgctgacagc | 360 |
| agtgcccaca gtacgccctc aactcccgtt gacagcagtg cccacagtac gccctcgact | 420 |
| cccgctgaca gcagtgccca cggtacgccc tcgactcccg ttgacagcag tgcccacagt | 480 |
| acgccctcaa ctcccgctga cagcagtgcc aatggtacgg ttttgatttt gcccgatggc | 540 |
| gctgcacttt ccacctttc gggcggaggg cttcttctgt gtgcgtgtgc tttgctgctg | 600 |
| cacgtgtttt ttacggcagt tttttctga tgt | 633 |

<210> SEQ ID NO 4
<211> LENGTH: 209
<212> TYPE: PRT
<213> ORGANISM: Trypanosoma cruzi

<400> SEQUENCE: 4

Ser Ala His Gly Thr Pro Ser Thr Pro Val Asp Ser Thr Ala His Gly
1               5                   10                  15

Thr Pro Ser Thr Pro Ala Asp Ser Ser Ala His Ser Thr Pro Ser Thr
            20                  25                  30

Pro Ala Asp Ser Ser Ala His Ser Thr Pro Ser Thr Pro Val Asp Ser
        35                  40                  45

Ser Ala His Ser Thr Pro Ser Thr Pro Ala Asp Ser Ser Ala His Ser
    50                  55                  60

Thr Pro Ser Thr Pro Ala Asp Ser Ser Ala His Ser Thr Pro Ser Thr
65                  70                  75                  80

Pro Val Asp Ser Thr Ala His Gly Thr Pro Ser Thr Pro Ala Asp Ser
                85                  90                  95

Ser Ala His Ser Thr Pro Ser Thr Pro Val Asp Ser Ser Ala His Ser
            100                 105                 110

Thr Pro Ser Thr Pro Ala Asp Ser Ser Ala His Ser Thr Pro Ser Thr
        115                 120                 125

Pro Val Asp Ser Ser Ala His Ser Thr Pro Ser Thr Pro Ala Asp Ser
    130                 135                 140

Ser Ala His Gly Thr Pro Ser Thr Pro Val Asp Ser Ser Ala His Ser
145                 150                 155                 160

Thr Pro Ser Thr Pro Ala Asp Ser Ser Ala Asn Gly Thr Val Leu Ile
                165                 170                 175

Leu Pro Asp Gly Ala Ala Leu Ser Thr Phe Ser Gly Gly Leu Leu
            180                 185                 190

Leu Cys Ala Cys Ala Leu Leu Leu His Val Phe Phe Thr Ala Val Phe
        195                 200                 205

Phe

<210> SEQ ID NO 5
<211> LENGTH: 2556
<212> TYPE: DNA
<213> ORGANISM: Artificial Sequence
<220> FEATURE:
<223> OTHER INFORMATION: Fusion of Trypanosoma cruzi Trans-sialidase and
      SAPA DNA sequences

<400> SEQUENCE: 5

| | |
|---|---|
| atgctggcac ccggatcgag ccgagttgag ctgtttaagc ggcaaagctc gaaggtgcca | 60 |
| tttgaaaagg acggcaaagt caccgagcgg gttgtccact cgttccgcct ccccgccctt | 120 |
| gttaatgtgg acggggtgat ggttgccatc gcggacgctc gctacgaaac atccaatgac | 180 |
| aactcccctca ttgatacggt ggcgaagtac agcgtggacg atggggagac gtgggagacc | 240 |

```
caaattgcca tcaagaacag tcgtgcatcg tctgtttctc gtgtggtgga tcccacagtg      300
attgtgaagg gcaacaagct ttacgtcctg gttggaagct acaacagttc gaggagctac      360
tggacgtcgc atggtgatgc gagagactgg gatattctgc ttgccgttgg tgaggtcacg      420
aagtccactg cgggcggcaa gataactgcg agtatcaaat gggggagccc cgtgtcactg      480
aaggaatttt ttccggcgga aatggaagga atgcacacaa atcaatttct tggcggtgca      540
ggtgttgcca ttgtggcgtc caacgggaat cttgtgtacc ctgtgcaggt tacgaacaaa      600
aagaagcaag ttttttccaa gatcttctac tcggaagacg agggcaagac gtggaagttt      660
gggaagggta ggagcgcttt tggctgctct gaacctgtgg cccttgagtg ggaggggaag      720
ctcatcataa acactcgagt tgactatcgc cgccgtctgg tgtacgagtc cagtgacatg      780
gggaattcgt ggctggaggc tgtcggcacg ctctcacgtg tgtggggccc ctcaccaaaa      840
tcgaaccagc ccggcagtca gagcagcttc actgccgtga ccatcgaggg aatgcgtgtt      900
atgctcttca cacccgct gaattttaag ggaaggtggc tgcgcgaccg actgaacctc      960
tggctgacgg ataaccagcg catttataac gttgggcaag tatccattgg tgatgaaaat     1020
tccgcctaca gctccgtcct gtacaaggat gataagctgt actgtttgca tgagatcaac     1080
agtaacgagg tgtacagcct tgttttgcg cgcctggttg gcgagctacg gatcattaaa     1140
tcagtgctgc agtcctggaa gaattgggac agccacctgt ccagcatttg cacccctgct     1200
gatccagccg cttcgtcgtc agagcgtggt tgtggtcccg ctgtcaccac ggttggtctt     1260 gttggcttt tgtcgcacag tgccaccaaa accgaatggg aggatgcgta ccgctgcgtg     1320
aacgcaagca cggcaaatgc ggagagggtt ccgaacggtt tgaagtttgc ggggttggc     1380 ggaggggcgc tttggccggt gagccagcag gggcagaatc aacggtatcg ctttgcaaac     1440
cacgcgttca ccgtggtggc gtcggtgacg attcacgagg ttccgagcgt cgcgagtcct     1500
ttgctgggtg cgagcctgga ctcttctggt ggcaaaaaac tcctggggct ctcgtacgac     1560
gagaggcacc agtggcagcc aatatacgga tcaacgccgg tgacgccgac cggatcgtgg     1620
gagatgggta agaggtacca cgtggttctt acgatggcga ataaaattgg ctccgagtac     1680
attgatggag aacctctgga gggttcaggg cagaccgttg tgccagacga gaggacgcct     1740
gacatctccc acttctacgt tggcgggtat aaaaggagtg atatgccaac cataagccac     1800
gtgacggtga taatgttct tctttacaac cgtcagctga atgccgagga gatcaggacc     1860
ttgttcttga gccaggacct gattggcacg gaagcacaca tggacagcag cagcgacacg     1920
agtgccagtg cccacggtac gccctcaact cccgttgaca gcactgccca cggtacgccc     1980
tcgactcccg ctgacagcag tgcccacagt acgccctcga ctcccgctga cagcagtgcc     2040
cacagtacgc cctcgactcc cgttgacagc agtgcccaca gtacgccctc gactcccgct     2100
gacagcagtg cccacagtac gcctcgact cccgctgaca gcagtcccca gtacgccc     2160 tcaactcccg ttgacagcac tgcccacggt acgccctcga ctcccgctga cagcagtgcc     2220
cacagtacgc cctcaactcc cgttgacagc agtgcccaca gtacgccctc gactcccgct     2280
gacagcagtg cccacagtac gccctcaact cccgttgaca gcagtgccca gtacgccc     2340 tcgactcccg ctgacagcag tgcccacggt acgccctcga ctcccgttga cagcagtgcc     2400
cacagtacgc cctcaactcc cgctgacagc agtgccaatg gtacggtttt gattttgccc     2460 gatgcgctg cactttccac cttttcgggc ggagggcttc ttctgtgtgc gtgtgctttg     2520
ctgctgcacg tgttttttac ggcagttttt ttctga                             2556
```

<210> SEQ ID NO 6
<211> LENGTH: 851
<212> TYPE: PRT
<213> ORGANISM: Artificial Sequence
<220> FEATURE:
<223> OTHER INFORMATION: Fusion of Trypanosoma cruzi Trans-sialidase and
      SAPA Protein sequences

<400> SEQUENCE: 6

```
Met Leu Ala Pro Gly Ser Ser Arg Val Glu Leu Phe Lys Arg Gln Ser
  1               5                  10                  15

Ser Lys Val Pro Phe Glu Lys Asp Gly Lys Val Thr Glu Arg Val Val
             20                  25                  30

His Ser Phe Arg Leu Pro Ala Leu Val Asn Val Asp Gly Val Met Val
         35                  40                  45

Ala Ile Ala Asp Ala Arg Tyr Glu Thr Ser Asn Asp Asn Ser Leu Ile
     50                  55                  60

Asp Thr Val Ala Lys Tyr Ser Val Asp Asp Gly Glu Thr Trp Glu Thr
 65                  70                  75                  80

Gln Ile Ala Ile Lys Asn Ser Arg Ala Ser Ser Val Ser Arg Val Val
                 85                  90                  95

Asp Pro Thr Val Ile Val Lys Gly Asn Lys Leu Tyr Val Leu Val Gly
            100                 105                 110

Ser Tyr Asn Ser Ser Arg Ser Tyr Trp Thr Ser His Gly Asp Ala Arg
        115                 120                 125

Asp Trp Asp Ile Leu Leu Ala Val Gly Glu Val Thr Lys Ser Thr Ala
    130                 135                 140

Gly Gly Lys Ile Thr Ala Ser Ile Lys Trp Gly Ser Pro Val Ser Leu
145                 150                 155                 160

Lys Glu Phe Phe Pro Ala Glu Met Glu Gly Met His Thr Asn Gln Phe
                165                 170                 175

Leu Gly Gly Ala Gly Val Ala Ile Val Ala Ser Asn Gly Asn Leu Val
            180                 185                 190

Tyr Pro Val Gln Val Thr Asn Lys Lys Lys Gln Val Phe Ser Lys Ile
        195                 200                 205

Phe Tyr Ser Glu Asp Glu Gly Lys Thr Trp Lys Phe Gly Lys Gly Arg
    210                 215                 220

Ser Ala Phe Gly Cys Ser Glu Pro Val Ala Leu Glu Trp Glu Gly Lys
225                 230                 235                 240

Leu Ile Ile Asn Thr Arg Val Asp Tyr Arg Arg Arg Leu Val Tyr Glu
                245                 250                 255

Ser Ser Asp Met Gly Asn Ser Trp Leu Glu Ala Val Gly Thr Leu Ser
            260                 265                 270

Arg Val Trp Gly Pro Ser Pro Lys Ser Asn Gln Pro Gly Ser Gln Ser
        275                 280                 285

Ser Phe Thr Ala Val Thr Ile Glu Gly Met Arg Val Met Leu Phe Thr
    290                 295                 300

His Pro Leu Asn Phe Lys Gly Arg Trp Leu Arg Asp Arg Leu Asn Leu
305                 310                 315                 320

Trp Leu Thr Asp Asn Gln Arg Ile Tyr Asn Val Gly Gln Val Ser Ile
                325                 330                 335

Gly Asp Glu Asn Ser Ala Tyr Ser Ser Val Leu Tyr Lys Asp Asp Lys
            340                 345                 350

Leu Tyr Cys Leu His Glu Ile Asn Ser Asn Glu Val Tyr Ser Leu Val
        355                 360                 365
```

```
Phe Ala Arg Leu Val Gly Glu Leu Arg Ile Ile Lys Ser Val Leu Gln
        370                 375                 380

Ser Trp Lys Asn Trp Asp Ser His Leu Ser Ser Ile Cys Thr Pro Ala
385                 390                 395                 400

Asp Pro Ala Ala Ser Ser Glu Arg Gly Cys Gly Pro Ala Val Thr
                405                 410                 415

Thr Val Gly Leu Val Gly Phe Leu Ser His Ser Ala Thr Lys Thr Glu
            420                 425                 430

Trp Glu Asp Ala Tyr Arg Cys Val Asn Ala Ser Thr Ala Asn Ala Glu
        435                 440                 445

Arg Val Pro Asn Gly Leu Lys Phe Ala Gly Val Gly Gly Ala Leu
450                 455                 460

Trp Pro Val Ser Gln Gln Gly Gln Asn Gln Arg Tyr Arg Phe Ala Asn
465                 470                 475                 480

His Ala Phe Thr Val Val Ala Ser Val Thr Ile His Glu Val Pro Ser
                485                 490                 495

Val Ala Ser Pro Leu Leu Gly Ala Ser Leu Asp Ser Ser Gly Gly Lys
            500                 505                 510

Lys Leu Leu Gly Leu Ser Tyr Asp Glu Arg His Gln Trp Gln Pro Ile
        515                 520                 525

Tyr Gly Ser Thr Pro Val Thr Pro Thr Gly Ser Trp Glu Met Gly Lys
530                 535                 540

Arg Tyr His Val Val Leu Thr Met Ala Asn Lys Ile Gly Ser Glu Tyr
545                 550                 555                 560

Ile Asp Gly Glu Pro Leu Glu Gly Ser Gly Gln Thr Val Val Pro Asp
                565                 570                 575

Glu Arg Thr Pro Asp Ile Ser His Phe Tyr Val Gly Tyr Lys Arg
            580                 585                 590

Ser Asp Met Pro Thr Ile Ser His Val Thr Val Asn Asn Val Leu Leu
        595                 600                 605

Tyr Asn Arg Gln Leu Asn Ala Glu Glu Ile Arg Thr Leu Phe Leu Ser
610                 615                 620

Gln Asp Leu Ile Gly Thr Glu Ala His Met Asp Ser Ser Ser Asp Thr
625                 630                 635                 640

Ser Ala Ser Ala His Gly Thr Pro Ser Thr Pro Val Asp Ser Thr Ala
                645                 650                 655

His Gly Thr Pro Ser Thr Pro Ala Asp Ser Ser Ala His Ser Thr Pro
            660                 665                 670

Ser Thr Pro Ala Asp Ser Ser Ala His Ser Thr Pro Ser Thr Pro Val
        675                 680                 685

Asp Ser Ser Ala His Ser Thr Pro Ser Thr Pro Ala Asp Ser Ser Ala
690                 695                 700

His Ser Thr Pro Ser Thr Pro Ala Asp Ser Ser Ala His Ser Thr Pro
705                 710                 715                 720

Ser Thr Pro Val Asp Ser Thr Ala His Gly Thr Pro Ser Thr Pro Ala
                725                 730                 735

Asp Ser Ser Ala His Ser Thr Pro Ser Thr Pro Val Asp Ser Ser Ala
            740                 745                 750

His Ser Thr Pro Ser Thr Pro Ala Asp Ser Ser Ala His Ser Thr Pro
        755                 760                 765

Ser Thr Pro Val Asp Ser Ser Ala His Ser Thr Pro Ser Thr Pro Ala
770                 775                 780
```

-continued

```
Asp Ser Ser Ala His Gly Thr Pro Ser Thr Pro Val Asp Ser Ser Ala
785                 790                 795                 800

His Ser Thr Pro Ser Thr Pro Ala Asp Ser Ser Ala Asn Gly Thr Val
                805                 810                 815

Leu Ile Leu Pro Asp Gly Ala Ala Leu Ser Thr Phe Ser Gly Gly Gly
            820                 825                 830

Leu Leu Leu Cys Ala Cys Ala Leu Leu Leu His Val Phe Phe Thr Ala
        835                 840                 845

Val Phe Phe
    850

<210> SEQ ID NO 7
<211> LENGTH: 12
<212> TYPE: PRT
<213> ORGANISM: Trypanosoma cruzi

<400> SEQUENCE: 7

Ala His Ser Thr Pro Ser Thr Pro Val Asp Ser Ser
1               5                   10
```

MULTICOMPONENT OR MONOCOMPONENT VACCINE TO BE USED AGAINST CHAGAS DISEASE, PHARMACEUTICAL COMPOSITIONS CONTAINING THEM, PROCEDURE FOR THE OBTENTION OF IMMUNOGEN OF SAID VACCINES, AND NUCLEIC ACID USED IN SAID PROCEDURE

The technical objective of this invention is to strengthen the immune response against protozoan and bacterial antigens, especially to increase the induction of the cytotoxic T response, essential against these antigens. This invention will lead to the development of therapeutic or prophylactic vaccine formulations for the Chagas disease.

STATE OF THE ART

*Trypanosoma cruzi* is a protozoan of the Kinetoplastida order, Tryponosomatidae family, distinguished by the presence of a single flagellum and a single mitochondrion, within which its genome is ordered in a complex and compact network called kinetoplast. It is an intracellular parasite with a life cycle involving vertebrates and invertebrates.

There are three different forms: Amastigote: spherical or oval, it is the reproductive form in the interior of the mammal cells, Epimastigote: elongated, with the kinetoplast located anterior to the nucleus, it is the reproductive form in the digestive tract of invertebrates and in culture media, and Trypomastigote: also elongated, but with the kinetoplast located posterior to the nucleus. Found in the mammals blood and is their infecting form. This form is not divided.

*T. cruzi* is divided in two large groups: *T. cruzi* I and *T. cruzi* II. The latter is divided into five smaller groups: *T. cruzi* IIa, IIb, IIc, IId and IIe.

The Chagas disease etiologic agent also known as American tripanosomiasis is a protozoan intracellular parasite, *Trypanosoma cruzi*. It is transmitted by a hematophagous insect, the *Triatoma infestans*, which transmits the parasite when the insect defecates on the bite wound as it feeds. On mammals the cycle of *T. cruzi* cycles between trypomastigote stage which circulates in the blood and the amastigote stage which replicates in the cytoplasm of infected host cells (especially on muscles). Chagas disease prevails in most Latin American countries including Mexico and Central America, where approximately 18 million people are infected with *T. cruzi* and at least 50.000 children and adults die every year from chronic Chagas disease due to lack of effective treatments.

The reduvid *triatoma*, known as vinchuca (from Ecuador to Patagonia), chipo (in Venezuela), pito (in Colombia), and barbeiro (in Brazil) are hematophagous insects, that is to say, blood suckers, that live in cracks, holes and dirty areas in houses or cellars in South America and Central America regions. They become infected after biting an animal or person that already suffers from the disease. In general, the infection is spread to human beings when an infected insect deposits feces on a person's skin while the person is sleeping at night.

The person often rubs the bite accidentally introducing feces in the bite wound, an open cut, eyes or mouth. Animals can also be infected in the same way and also contract the disease eating the infected insect. The infected person may not present symptoms of the disease until 10 or 15 years after being infected; this makes the detection of the disease even more difficult.

More than 90 million people are at risk of infection in endemic areas. In addition, in the endemic areas, 2-5% of fetus carried by infected mothers are aborted or born with the congenital Chagas disease.

Loss of revenue in terms of productivity lost due to sickness and high medical costs have an overwhelming effect in the economic growth of these countries. The risk of transmission of *T. cruzi* to non-infected individuals through organ transplants and blood transfusions from infected immigrant donors is very high.

Chemotherapeutical treatments have been partially successful in controlling *T. cruzi* infection and Chagas disease. However, the high toxicity of drugs and poor efficacy of available therapeutics has limited the use of chemotherapy for treatment of both acute and chronic patients. Further, drug therapy reduces the severity of disease in chronically infected individuals but cannot reverse the damage already done by parasites.

There are practically no vaccines for the prevention or treatment of the *T. cruzi* infection. Traditional vaccines constituted of heat-inactivated parasites, or subcellular fractions of the *T. cruzi* provide a degree of protection for *T. cruzi* infections (M. Basombrio, Exp. Parasitol. 71:1-8 (1990); A. Ruiz et al., Mol. Biochem. Parasitol, 39:117-125. (1990)). However, these vaccines fail to elicit the protective level of immunity, probably due to loss of important epitopes during inactivation and/or the failure of the antigens to enter the Major Histocompatibility Complex (MHC) class I pathway of antigen processing and presentation, and to elicit cell mediated immune responses (J. Mónaco. Immunol. Today 13:173-179 (1992)). Live attenuated vaccines are capable of entering the MHC class I pathway and might elicit protective immune responses. However, the danger of reversion of the attenuated parasites to virulent strains if attenuation is not been completed renders these vaccines impracticable. A DNA vaccine containing the gene codifying a trans-sialidase has been shown to provide prophylactic protection against *T. cruzi* infections in mice (F. Costa et al, Vaccine 16:768-774 (1998)), but has not been shown to prevent or reverse disease or to stimulate a CD8+ T cell response in animals. In addition, the specific cellular and humoral immune response in BALB/c mice immunized with an expression genomic library of the *T. cruzi* was observed (E. Alberti et al., Vaccine 16:608-612 (1998)).

Trans-sialidase is a *Trypanosoma cruzi* enzyme (agent that causes Chagas disease) required by this parasite to invade cells of the human host. Given the fact that if the parasite does not invade cells, it will not survive in humans, trans-sialidase seems the ideal target for an immunological attack, that is, to develop a vaccine. Therefore, the objective is a vaccine that as a response when used to immunize, may produce antibodies specifically inhibiting the trans-sialidase.

There are several trans-sialidases produced in the trypanosome. Some have only one region required for the enzymatic activity (the trans-sialidation which is the transfer of a sugar called sialic acid). Others, in addition to this region have a second region not related to trans-sialidation but that is very immunogenic (it generates antibodies in the host). This second region is called SAPA (Shed-acude-phase-antigen) and is formed by repetitive units of amino acids.

The gens (nucleic acids, DNA, formed by units called nucleotides or bases, a region of the DNA that codifyings a protein as in this case trans-sialidase, is called gen) codifying the region with enzymatic activity and the SAPA region have been identified.

One of the *T. cruzi* molecules described as essential for the host cell invasion is the sialic acid (Schenkman S. Et al. Cell 65, 1117-1126, 1991; Schenkman, S. et al. Ann. Rev. Microbiol. 48, 499-523, 1994; Schenkman, S. and Eichinger, D. Parasitology Today 9, 218-222, 1993). Since trypanosome is unable to synthesize sialic acid (Schauer, R. y et al. Z. Physiol. Chem. 364: 1053-1057, 1983), it must obtain it from molecules containing sialic acid present in the environment. This process is accomplished using a unique enzyme called trans-sialidase (Previato, J. O. et. al., Mol. Biochem. Parasitol. 16:8596, 1985 Y Zingales, B., et al., Mol. Biochem. Parasitol. 26, 135-144, 1987). Trans-sialidase is capable of transferring sialic acid from sialydated molecules present in the environment, such as some molecules found in the blood of the infected host, to molecules present on the trypanosome surface.

Trypanosome molecules that can be sialylated are those called mucins (Ruiz, R. C., et al. Parasite Immunol. 15,121-12, 1993; M. B. Reyes, et al. Gene 140, 139-140, 1994; J. M. Di Noia et al. J. Biol. Chem. 270, 24146-24149, 1995; J. M. Di Noia, et al. J. Biol. Chem. 271, 32078-32083, 1996). Once sialylated, mucins are the molecules that interact with the surface of the human cell to be invaded, facilitating the infection process (Ruiz, R. C., et al. Parasite Immunol. 15, 121-12, 1993). Other groups have demonstrated that if the parasite does not express trans-sialidase, it cannot infect cells in the same way as parasites containing trans-sialidase do (Pereira et al., Infect. Immum. 64, 38843892, 1996). Therefore, immunization with trans-sialidase made in such a way that generates antibodies to inhibit the enzyme, constitutes a useful tool to obtain a vaccine against this parasite. Recently it has been demonstrated that the immune response against trans-sialidase is a factor that helps prevent death of the host caused by the parasite ((Chuenkova, M. y Pereira M. E. A., J. Exp. Med. 181, 1693-1703, 1995).

*Trypanosoma cruzi* has two types of trans-sialidases. One type contains only the amino acids required for the activity of trans-sialidase (Briones, M. R. S. et al. Mol. Biochem. Parasitol. 70: 9-17, 1995) and was used in the application WO 9318787 with the purpose to synthesize carbohydrates due to its enzymatic activity and was proposed in second place as an immunogen in the same patent application. A second group of trans-sialidases contains, in addition to these sequences, a series of amino acid repetitions in the terminal carboxyl region called SAPA (C. Ibáñez, et al. Mol. Biochem. Parasitol. 30: 27-34, 1988; J. L. Affranchino, et al. Mol. Biochem. Parasitol 34: 221228, 1989; Cazzulo, J. J. and Frasch, A. C. C. FASEB J. 6, 3259326, 1992). This second region is highly antigenic during a natural infection in humans (M. B. Reyes, et al., Proc. Natl. Acad. Sci. USA 87:2846-2850, 1990).

The broader investigations for vaccines have been focused on attempts to develop prophylactic protein vaccines against the infection of *T. cruzi*, but have been carried out with little success. The development of vaccines of subunits composed by defined antigens capable of inducing strong humoral and class 1 T cell responses and of reducing the parasite burden, has been hindered due to lack of knowledge of biology of the three developing stages of the *T. cruzi*, the absence of sufficient information of the sequence on gens expressed in the contagious and intracellular stages, and the scientific view that chronic disease is not related to persistent parasite infection but it is the result of a parasite-induced autoimmune response.

SUMMARY OF THE INVENTION

The first object of the present invention is a vaccine against Chagas disease, capable of stimulating the immune response against the trans-sialidase virulence factor of the parasite *Trypanosoma cruzi*, the vaccine is distinguished by the fact that it comprises a multicomponent vaccine for the Chagas disease (American tripanosomiasis) comprising: (a) an immunogenic portion formed by one or more recombinant or synthetic polypeptides or fractions thereof and (b) one or more polynucleotides comprising the regions that codifies one or more immunogenic polypeptides, both portions for the *Trypanosoma cruzi* derivates (i.e., *T. cruzi* and or a conserved region common to many of them) where the vaccine administration is a protection against the parasite infection, eliminates it or reduces the clinical consequences of the infection.

Another objective of the present invention is a monocomponent vaccine against the Chagas disease that comprises at least one component selected among an immunogenic portion formed by one or more recombinant or synthetic polypeptides or fractions thereof, and a group of polynucleotides including the regions that codifying one or more immunogenic polypeptides derived from *Trypanosoma cruzi* (i.e. a *T. cruzi* and/or a conserved region common to many of them) where the immunogenic portion or the polynucleotides group stimulates an antibody response, of CD4+ Th1 biased T cells or CD8+ T cells against the *Trypanosoma cruzi*.

This invention also includes the pharmaceutical compositions containing the multicomponent and monocomponent vaccines, the procedures for the obtention of the immunogen portion of said vaccines and the nucleic acid used in said procedure.

FIGURES DESCRIPTION

FIG. 1: SEQ ID NO: 1. Sequence of the nucleotides of the gene region codifying the *Trypanosoma cruzi* protein having trans-sialidase activity. Letters represent four bases (molecules) that constitute de DNA (deoxyribonucleic acid). A: adenine, T: tymine, C: cytokine, G: guanine Every three bases (bases triplet) codifies an amino acid (molecular unit faulted by the protein) that in this case is trans-sialidase. The ATG indicated in low case is the first amino acid of the trans-sialidase (methionine amino acid). The last TGA triplet is the one used by the cell to indicate where the protein ends (termination triplet).

FIG. 2: SEQ ID NO: 2. Amino acid sequences of the region codified by the gene of SEQ ID NO: 1 showed in FIG. 1 and that corresponds to the part of the protein having trans-sialidase activity. Each letter indicates an amino acid according to the universally accepted code.

FIG. 3: SEQ ID NO: 3. Base sequence codifying the region of repetitive units of amino acids called SAPA. Remaining instructions same as SEQ ID NO: 1 shown in FIG. 1.

FIG. 4 SEQ ID NO: 4. Amino acids sequence codifying according to the base sequence of SEQ ID NO: 3 indicated in FIG. 3 and corresponding to SAPA protein.

FIG. 5: SEQ ID NO: 5. Nucleotides (upper line) and amino acid (lower line) sequence corresponding to the gene and the protein respectively, resulting from the union of trans-sialidase and SAPA.

DETAILED DESCRIPTION OF THE INVENTION

The present invention provides an efficient vaccine for treating or avoiding the infection of a mammal by *Trypanosoma cruzi* derivatives (i.e. *T. cruzi* and/or a conserved region common to many of them). In a preferred embodiment, the vaccine is effective against infection and/or illness caused by *T. cruzi*. The multicomponent vaccine of this invention is for the Chagas disease (American tripanosomiasis) comprising: (a) an immunogenic portion formed by one or more recombinant or synthetic polypeptides, or fractions thereof, and (b) one or more polynucleotides including the regions that codifying one or more immunogenic polypeptides, both portions for the *Trypanosoma cruzi* derivates (i.e., *T. cruzi* and or a conserved region common to many of them) where the vaccine administration is a protection against the parasite infection, eliminates it or reduces the clinical consequences of the infection. One polynucleotide vaccine contains one or more polynucleotides that comprise the regions codifying one or more immunogenic polypeptides derived from *T. cruzi*. In a similar way, a polypeptide vaccine contains one or more immunogenic polypeptides derived from *T. cruzi*.

Another objective of this invention is a monocomponent vaccine against Chagas disease comprising at least one component selected between one immunogenic portion is selected from one or more recombinant or synthetic polypeptides, or fractions thereof, and a group of polynucleotides that cover the regions that codifying one or more immunogenic polypeptides derived from the *Trypanosoma cruzi* (i.e., of a *T. cruzi* and/or a conserved region common to many of them) where the immunogenic portion stimulates an antibody response of CD4+ Th1 biased T cells or CD8+ T cells against *Trypanosoma cruzi*.

The "immunogenic portion" of the vaccine may comprise one or more polypeptides, the structure of which includes a C-terminal region which consists of at least two repetitive units; each of those repetitive units shows at least 60% homology to the following amino acid sequence: AHSTP-STPVDSS (SEQ ID NO: 6) and a polypeptide with trans-sialidase activity is fused to the C-terminal region. It may also comprise an adjuvant which does not destroy the trans-sialidase enzymatic activity of the immunogen portion, preferably aluminum oxide. The portion may comprise between 10 and 16 repetitive units in the C-terminal region, preferably 13 units.

The immunogenic portion may be obtained from the *Trypanosoma cruzi* trypomastigotes (i. e. from a *T. cruzi* and/or a conserved region common to many of them).

This invention relates to a vaccine that may be a recombinant biomolecule formed by the fusion of that region which consists of repetitive units of amino acids and the polypeptide with trans-sialidase activity and/or the polypeptide with cysteine proteinase activity, and/or the Paraflagelar Rod Proteins (PFR).

The multicomponent vaccine of this invention preferably stimulates an antibody response or an immune response transmitted through cells, or both responses, in the mammal to which the vaccine will be administered. The vaccine preferably stimulated a response of CD4+ Th1 biased T cells or CD8+ T cells. Preferably in the case of a monocomponent vaccine, the vaccine stimulates the antibody response, a response of CD4+ Th1 biased T cells or a response of the CD8+ T cells. A form of especially preparing the vaccine of this invention includes a nucleotide comprising the regions codifying a cytokine, to provide the additional stimulation to the mammal immune system. In a preferred embodiment, the preparation of the vaccine of this invention includes an immunogenic polypeptide which contains a sequence of membrane displacement, to facilitate the introduction of the polypeptide in the mammal's cell and the subsequent stimulation of the immune response transmitted through cells.

The immunogen of this invention may be selected from the TSA-1, ASP-1, ASP-2, hemolysin and Lyt1 proteins.

The multicomponent vaccine of this invention may comprise a plurality of polynucleotides that comprise the regions codifying one or more immunogenic polynucleotides derived from the *T. cruzi* (of a *T. cruzi* and/or a conserved region common to many of them) and at least one or more polynucleotides comprising the regions codifying the cytokines that may be selected among interleukin 12 (IL-12), granulocyte-macrophage colony-stimulating factor (GM-CSF), interleukin 6 (IL-6), interleukin 18 (IL-18), γ-interferon, α,β-interferons and chemokines; the IL-12 and GM-CSF cytokines are especially preferred.

The pharmaceutical compositions that contained the recombinant or synthetic polypeptides, or fractions of the immunogenic portion and the polynucleotides including the regions which codifying one or more immunogenic polypeptides derived from the *T. cruzi*, together with a pharmaceutical carrier are also the object of this invention.

In another embodiment, this invention also provides a vaccine of multiple polynucleotide components. It is prepared by inserting two or more nucleotides comprising the regions which codifying one or more immunogenic polypeptides derived from the *T. cruzi* in two or more polynucleotide vectors, later combining the polynucleotide vectors to yield a polynucleotide vaccine.

Alternatively, this invention related vaccine may be prophylactically administered to a mammal before the *T. cruzi* infection. In a preferred embodiment the vaccine application must be efficient to prevent the subsequent infection of the mammal with *T. cruzi*. In another embodiment the vaccine administration is efficient to prevent the development of the chronic debilitating disease in a mammal after the subsequent infection with *T. cruzi*. In other embodiment, the vaccine application is efficient to prevent mammal's death after the subsequent infection with *T. cruzi*.

In another embodiment, the invention includes a method for identify the immunogenic polypeptides of *T. cruzi* from a *T. cruzi* library, to be used in a polynucleotide vaccine. In a preferred embodiment, the procedure utilizes the expression library immunization (ELI) in mice to identify the *T. cruzi* polypeptides that elicit an immune response in a mammal effective to prevent the death, arrest or delay the progression of disease in the mammal that has been infected with *T. cruzi*. The method is preferably used to identify the immunogenic polypeptides derived from the *T. cruzi* and from the BALB/c or B6 mice which have been immunized.

In another embodiment the method involves the following:
(a) preparing a DNA microarray comprising open reading frame of *T. cruzi* genes;
(b) preparing a first probe comprising Cy3-labeled trypomastigote-derived *T. cruzi* cDNA;
(c) preparing a second probe comprising Cy5-labeled amastigote-derived cDNA;
(d) cohybridizing the first and second probes to the microarray to identify at least one gene whose expression is the *T. cruzi* during the intracellular amastigote stage of the infectious cycle, where the gene codifies a candidate immunogenic *T. cruzi* polypeptide; and
(e) immunizing mice with the gene to determine whether the gene codifies a *T. cruzi* polypeptide that elicits an immune response in a mammal effective to prevent the death of the mammal or to arrest or delay the progression of disease in the mammal associated with infection of the mammal by *T. cruzi*.

A form of preparing the immunogen used in the multicomponent or monocomponent vaccines of this invention comprises the following steps: a) bindung the codifying nucleotidic sequences for the immunogenic peptide/s to a vector capable of expressing such sequence, b) linking the codifying sequence obtained in the previous step to a vector capable of expressing such sequence, c) transforming a host capable of expressing the codifying sequence of the immunogen, d) growing the transformed bacteria obtained in the previous step in an appropriate culture medium, e) isolating and purifying the immunogen obtained in the previous step.

Stage b) vector may be pET22b+. The hosts are eukaryote cells, bacteria, especially *Escherichia coli* BL26DE3, and yeasts. The culture medium of stage d) may be an L-Broth medium.

Another form of preparing the immunogen used in the multicomponent or monocomponent vaccines of this invention comprises the following stages: a) growing trypomastigote form of *Trypanosoma cruzi* in an adequate culture medium, b) obtaining the supernatant where the trypomastigote forms have grown by centrifugation at 5000 rpm during 10 minutes, c) filtrating the supernatant obtained and passage through an affinity column containing immunoglobulins that recognize the repetitions of the carboxymethyl terminal sequence of the immunogen, d) eluting increasing the pH to detach the protein.

Peptides used in the procedures of this invention may be obtained by chemical synthesis.

Another object of this invention comprises a nucleic acid used in the procedures previously explained because it essentially comprises a sequence codifying said immunogen.

Over 100 natural mammalian hosts are known for *T. cruzi*-hosts, and *T. cruzi* can be transmitted to a human from another animal host. Any mammalian host can be immunized according to this invention. Vaccine administration in this application includes humans, domestic animals such as dogs and cats, rodents and wildlife animals. Preferably, the mammal that is immunized is a dog, a cat or a human.

Polynucleotide Vaccine

The polynucleotide vaccine of the invention includes at least one, preferably at least two, nucleotides coding regions, each coding regiong encoding an immunogenic polypeptide component from *T. cruzi*. When it contains two or more nucleotide coding regions, the polynucleotide vaccine is referred to herein as multicomponent vaccine. It is convenient to minimize the number of different immunogenic polypeptides encoded by the nucleotide coding regions; however, considering that a polynucleotide vaccine generates the highest level of protection, it will codifie 10 or more immunogenic polypeptides. The polynucleotide vaccine contains DNA, RNA, a modified nucleic acid, or any combination thereof. Preferably, the vaccine comprise one or more expression or cloning vectors; more preferably, the vaccine comprises a plurality of expression vectors capable of autonomous expression of a nucleotide coding region in a mammalian cell to produce at least one or more immunogenic polypeptides or cytokine. An expression vector preferably includes a eukaryote promoter sequence, more preferably the nucleotide sequence of a strong eukaryotic promoter operatibly linked to one or more coding regions. A promoter is a DNA fragment which acts as a regulatory signal and binds the RNA polymerase in a cell to initiate the transcription of a downstream (direction 3') coding sequence; the transcription is the formation of an RNA chain in accordance with the genetic information contained in the DNA. A promoter is operatibly linked to a nucleic acid sequence, or may be used to control or regulate the transcription of that nucleic acid sequence. This invention is not limited to a specific eukaryotic promoter but extends to the wide variety known; preferably, the expression vector includes a CMV or RSV promoter. The promoter used preferably remains as constitutive promoter.

A vector useful in the present invention can be circular or linear, single-stranded or double-stranded and can be a plasmid, cosmid or eposome but is preferably a plasmid. In a preferred embodiment, each nucleotide coding region (whether it codifies an immunogenic polypeptide or a cytokine) is on a separate vector; however, it is to be understood that one or more regions can be present on a single vector, and these regions can be under the control of single or multiple promoters.

Nucleotidic sequences codifying cytokines may be added to the polynucleotide vaccine, such as a granulocyte-macrophage colony-stimulating factor (GM-CSF), interleukin 12 (IL-12) and the co-stimulating molecules, such as B7-1, B7-2, CD40. Cytokines may be used in several combinations to fine tune the response of the animal's immune system, including both antibody and cytotoxic T lymphocyte responses, achieving a specific level of response needed to control or eliminate the *T. cruzi* infection. The polynucleotide vaccine may include a fusion product containing an antigenic polypeptide and a molecule, such as CTLA-4, which directs the fusion product to the cells with antigen presence within the host.

Plasmids and other delivery systems are prepared using well known techniques in molecular biology. This invention may include procedures to prepare and use the polynucleotide vaccine.

Polypeptide Vaccine

The polypeptide vaccine of this invention includes at least one—preferably at least two—immunogenic polypeptides from *T. cruzi* (recombinant or synthetic, or fractions thereof). As with the polynucleotide vaccine, it is desirable to minimize the number of different immunogenic polypeptides supplied in the vaccine; however, it is nonetheless contemplated that a polypeptide vaccine that generates the highest level of protection will contain IQ or more numerous immunogenic polypeptides.

Because a CD8+ T cells response cannot normally be directly triggered by the administration of a conventional protein subunit vaccine, the immunogenic polypeptides contained in the polypeptide vaccine include preferably include one or more membrane transporting sequences (MTS) fused to their N-terminus or C-terminus or both. A membrane transporting sequence allows for transport of the immunogenic polypeptide across a lipid bilayer, allowing it to be delivered to the inside of a mammalian cell.

Cytokines

The Cytokines are proteins which regulate the function of the cells that produce them or other cellular types. They are the agents responsible for intercellular communication; they induce the activation of membrane specific receptors, proliferation functions and cellular differentiation, chemiotaxis, growth and modulation of immunoglobulin secretion. They are basically produced by activated lymphocytes and macrophages, although they may also be produced by polynuclear leukocytes, endotelial cells, epitelial cells and conjunctive tissue cells. Depending on the cell that produces them, they are called lymphokines (liymphocyte), monocynes (monocyte) or interleukines (hematopoietic cells). Their basic action is the regulation of the inflammation mechanism. There are pro-inflammatory and anti-inflammatory cytokines.

Preferably, the polynucleotide vaccine includes at least one nucleotide coding the region codifying a cytokine. Preferred cytokines include interleukin 12 (IL-12), granulocyte-macrophage colony-stimulating factor (GM-CSF), interleukin 6 (IL-6), interleukin 18 (IL-18), γ-interferon, α,β-interferons, and chemokines. Especially preferred cytokines include IL-12 and GM-CSF.

Pharmaceutical Compositions

The polynucleotide and polypeptide vaccines of the invention are readily formulated as pharmaceutical compositions for veterinary or human use. The pharmaceutical composition optionally includes excipients or diluents that are pharmaceutically acceptable such as those that were compatible with the genetic material. The term "pharmaceutically acceptable carrier" refers to a carrier that is acceptable in the sense that it is compatible with the various components of a composition and that does not negatively affect its therapeutical behavior. Suitable excipients are, for example, water, saline solution, dextrose, glycerol, ethanol, or the like and combinations thereof. In addition, if desired, the vaccine may contain minor amounts of auxiliary substances such as wetting or emulsifying agents, pH buffering agents, salts, and/or coadjuvants that enhance the effectiveness of the stimulating composition of an immune response. In this invention some procedures to prepare and use those pharmaceutical compositions are also included.

Administration of a Combination of a Polynucleotide Vaccine and of the Polypeptide Vaccine This invention comprises the administration of a polynucleotide vaccine and of a polypeptide vaccine to a mammal in a serial protocol. For example, a plasmid-based DNA vaccine may be administered to the primary immune system of a mammal, followed by one or more administrations of a polypeptide vaccine or of a viral vaccine (for example, vector of the vaccine polypeptide that carries the genes that codifies the immunogenic polypeptides and, optionally, the cytokines) to stimulate the mammal's immune system. The order of administration of the various types of vaccines and the nature of the vaccines administered, in any dosage (for example the polypeptide vaccine, plasmid vaccine, viral vector vaccine) may be easily determined by an expert to provoke the most efficient immune response in the mammal.

Definitions of Certain Words and Expressions

"Chagas disease" refers to different clinical expressions in patients infected by different varieties of the *T. cruzi*, related at the same time to the chronic immunological impact on various white tissues. Consequently, vaccines presently known, either from monkeys or multicomponents from frequently available substances of some *T. cruzi* type, are partial formulas to undertake a potentially effective treatment in every geographical area where this disease develops, and against every intra o extra-cellular form of the parasite. In addition, the immunogenicity of such common components may vary over time and/or with changes in the host health condition, and therefore, a universal continuous protection is not guaranteed.

"T Lymphocyte" refers to cells (white blood cells) in charge of coordinating the cell-mediated immune response, as well as cooperation functions for the development of every kind of immunological responses, including antibodies response by B lymphocytes. T lymphocytes may be differentiated from B lymphocytes and killer cells due to the appearance of a special receptor in the surface of the membrane, named T-cells Receptor (TCR). T comes from thymus, the most important organ for the differentiation of these cells from mother cells of the lymphatic system.

"CD4+ T cell" refers to T lymphocytes responsible for coordinating cell-mediated immune response, as well as cooperation functions for the development of every kind of immunological response, including antibodies response by B lymphocytes.

"CD8+ T cell" refers to Cytotoxic T Lymphocytes T (CTL); they are included in the T lymphocytes line responsible for the effector function of cell immunity. They neutralize cells infected by intracellular microorganisms, by attacking directly infected cells, injecting toxic enzymes and destroying them. They are currently named CD8+, due to the presence of the CD8 membrane receptor.

CTLs are essentially able to lyse cells when stimulated adequately, especially by antigens expressed on MHC class I. Very specific in their lethal functions, they have the ability to destroy a target cell without affecting surrounding uninfected cells. The cell CTL-mediated destruction process comprises:

Recognition of foreign antigen and formation of a stable conjugate with membrane receptors; MHC-I, TCR, CD8, ICAM-1, LFA-1, among other receptors and co-stimulators;

to Activation of CTL cell by means of cell interrelations mediated by membrane proteins and transduction of intracellular signs;

Cell lysis compelling to changes in target's cell and exocytosis of poisoning granules containing principally perforin y granzine;

Apoptosis of the target cell including the mediation of molecules inducing cell death, like Fas and its ligand.

Due to the high toxicity of these lymphocytes, and in order to prevent the unnecessary risk of continuous circulation, inactive or virgin cytotoxic cells require two types of triggering signals:

Binding of T cells receptor in the membrane of the cytotoxic cell to Major Histocompatibility Complex (MHC-I) type I on the surface of cells presenting antigen (CPA), Cells infected by microorganisms, preferably intracellular ones (like viruses), show remnants of the microorganism on their surface in the context of a MHC-I molecule. The infected cell shows antigens foreign to a CPA that processes infecting information to CTLs, Co-stimulation at high concentrations derived from the binding between CD40 molecule appearing on membranes of dendritic cells and their ligand (CD40L) of cytotoxic cells. It is a redundant interaction, that is to say, the more contacts between CD40 and its ligand, the greater is the production of ligands by the CTL, turning triggering signal stronger and more definitive.

In infected tissues, CTLs recognizing the antigen involved are activated and retained in the infection area, and they carry out their effector activity. Those CTLs not recognizing the antigen involved return to circulation.

The "Immunogenic polypeptide" used in the vaccine against *T. cruzi* according to this invention refers to the one that can be expressed by *T. cruzi* in extracellular stage (trypomastigote), in intracellular stage (amastigote), or during both stages of the life cycle. Preferably, the immunogenic polypeptide is expressed by the *T. cruzi* amastigote in early stage of infection, in approximately 24 hours after initial infection.

A type of polypeptides exemplifying immunogenic polypeptides according to the invention is from the family of the trans-sialidase proteins, such as TSA-1 (*T. cruzi* Peru; D. Fouts et. al. Mol. Biochem. Parasitol. 46:189-200 (1991);

GenBank. Acc. Number M58466), ASP-1 (*T. cruzi* el Brazil; M. Santos et al. Mol. Biochem. Parasitol. 86:1-11 (1997): GenBank. Acc. Number U74494)) and ASP-2 (*T. cruzi* el Brazil; H. Low et al. Mol. Biochem. Parasitol. 88:137-149 (1997); GenBank. Acc. Number U77951).

Advantages of this Invention

This invention is the most complete multicomponent or monocomponent vaccine that may constitute varieties of the same component of different *T. cruzi*, especially of those portions conserved and/or with the addition of targets different among them, for example taking as a target one or several trans-sialidases, fragellar proteins or cysteine proteases from one or more varieties of *T. cruzi*.

Chagas is a disease requiring incentives and protection for the development and distribution investments; therefore there is no room for a competitive, multi-optional market, as if an Argentine vaccine, a Brazilian vaccine, a Peruvian vaccine, etc. co-existed; in practice, presently known vaccines could not be developed without leaving unprotected an important part of the population affected. Consequently the invention involves the maximum immunogenicity combination facing the variety of clinical expressions (that is, a "monoshot-continental" vaccine).

A formula is proposed to be used against all varieties and clinical expressions. Formulas with such wide range of multicomponents have not been described up to this date.

Advantages of a Genetic Vaccine

Choosing the administration of the polynucleotide as an immunization technique offers an excellent advantage over the different systems that supply other vaccines or antigen delivery systems. Vaccines containing genetic material are preferred over traditional vaccines because vectors are easy to construct and produce, the potential for the modification of mutagenesis sequences directed to enhance antigenic potency of individual epitopes, or to abolish epitopes that might trigger an unwanted response. In the case of DNA vaccines, DNA stability, the lack of the risks associated to live and attenuated vaccines, their ability to induce humoral immunity and cell transmitted immunity, and, particularly, CD8+ T cell responses, and persistence of the immunity responses.

It has also been demonstrated their ability to improve immunity response by the co-administration of genes codifying cytokines.

TABLE 1

TS activity in serum following intravenous injection of trans-sialidase protein (TS) or SAPA-bound trans-sialidase (TS-SAPA).

| | Hours post-inoculation | | | |
|---|---|---|---|---|
| | 0.5 | 16 | 26 | 110 |
| TS* | 100% | 3% | 0% | 0% |
| TS-SAPA* | 100% | 60% | 50% | 5% |

Values are averages obtained from three independent animals per group. Measuring was carried out on serum samples collected from each mouse at 30 minutes, and 16, 26 and 110 hours following inoculation. The mouse strain used was C3H.
*Values expressed in % activity of remaining trans-sialidase considering as 100% the values obtained 0.5 h following TS immunization (for TS values) or with TS-SAPA (for TS-SAPA values) respectively.

If instead of injecting a protein with trans-sialidase activity, a mouse is intravenously injected a protein containing the region with trans-sialidase activity bound to SAPA protein (TS-SAPA), results obtained are different (Table 1). When samples are collected at different times following intravenous injection, trans-sialidase activity is detectable up to 5 days after the injection. These results show that SAPA protein, when bound to another protein like trans-sialidase, is conferred a new property: the property of stabilizing it in blood, maintaining this enzymatic activity in circulation for a longer time.

Results similar to those described above may be obtained when other routes of administration, such as, intramuscular, intraperitoneal, subcutaneous or any other triggering an antibody response in the immunized host are used instead of the intravenous route of administration. Similar results can be obtained as well when some of the already known immunizing adjuvants are used, such as aluminum oxide or others not destroying the enzyme, as detailed below. An adjuvant is either an oily or aqueous substance, or a substance with another structure that injected jointly with the immunogen—in this case a recombinant protein like trans-sialidase/SAPA-contributes to increase immunogenicity, that is, increases the immune system response related to antibodies production or cell response. A cell response is a type of response by the immunologic system where basically the cells contributing to control an infectious agent proliferate.

Another result obtained from these experiments is that a response against trans-sialidase inhibiting its activity is only obtained when this enzyme is used as an immunogen in its active form, that is, with a conformation that retains its enzymatic activity.

TABLE 2

Inhibiting activity of the trans-sialidase in serum of animals immunized with trans-sialidase, with repetitions (TS-SAPA), with Freund's adjuvant (AF), with aluminum oxide ($Al_2O_3$) or with protein denaturalized by heat at 80° C. (80° C.) Immunization was carried out by intraperitoneal route, in all cases with 65 nanogrames for the first dose (day 0) and with 13 nanogrames for the second dose on day 38. Trans-sialidase inhibition measure was carried out as described for the experiments previous to day 1 and on day 45 after the first immunization (day 0). The measure is expressed in % of the inhibition obtained in the presence of serum of non immunized mice, the inhibition values of which are considered 0. The values are the average obtained from four immunized mice independently for each condition.

| | Days after immunization | |
|---|---|---|
| | 1 | 45 |
| TS-SAPA in AF | 0% | 0% |
| TS-SAPA in $Al_2O_3$ | 0% | 90% |
| TS-SAPA at 80° C. | 0% | 0% |

Another result obtained as a consequence of these experiments is that only a response is obtained against the trans-sialidase that inhibits its activity when this enzyme is used as immunogen in its active formulation, that is, with such a conformation that it keeps its enzymatic activity. Table 2 shows that when the adjuvant used to immunize mice is aluminum oxide—which does not alter the enzymatic activity of trans-sialidase—antibodies which inhibit it are generated. However, if Freund is used as adjuvant—which destroys the enzymatic activity of trans-sialidase, no antibodies inhibiting trans-sialidase will be generated in the mouse. Likewise, heat-inactivated trans-sialidase at 80° C. for 3 minutes so as to avoid protein from maintaining it enzymatic activity, preventing it from being stimulated by the formation of neutralizing antibodies.

Results similar to those described above may be obtained when other routes of administration, such as intramuscular, intraperitoneal, subcutaneous or any other triggering an antibody response in the immunized host are used instead of the intravenous route of administration.

Furthermore, similar results may be obtained when some of the adjuvants known to immunize, such as aluminum oxide or others which do not destroy the enzyme, as mentioned before. An adjuvant is oily, water, or other structure substance, that injected together with the immunogen, in this case a recombinant protein, such as trans-sialidase/SAPA, contributes to increase its immunogenicity, that is, it increases the response of the immune system as regards antibodies production or cell response. Cell response is a type of response of the immunologic system where proliferation is basically of cells contributing to control an infectious agent.

There is no doubt that once this invention is put into practice, some modifications may be introduced regarding construction and shape details; this will not imply straying away from the fundamentals that are clearly expressed in the claims that follow.

I claim:

1. A monocomponent vaccine effective to moderate the clinical consequences of Chagas disease, said vaccine comprising, as active ingredient, an immunogenic component comprising a polynucleotide, said nucleotide encoding one or more polypeptide(s) each having a C-terminal region composed of at least two repetitive units of amino acids and a eukaryotic promoter operably linked to one or more coding regions for said polypeptide(s), wherein each repetitive unit of amino acids shows the following amino acid sequence:

AHSTPSTPVDSS (SEQ ID NO: 6)

and wherein a polypeptide with trans-sialidase activity of *Trypanosoma cruzi* is fused to the C-terminal region of each of said polypeptide(s), wherein the polypeptide with trans-sialidase activity of *Trypanosoma cruzi* has the amino acid sequence of SEQ ID NO. 2 and is encoded by the nucleotide sequence of SEQ ID NO. 1, and wherein the vaccine further comprises an adjuvant that does not inhibit trans-sialidase enzymatic activity of the immunogen portion, wherein the adjuvant is aluminum oxide.

2. The monocomponent vaccine of claim 1, wherein the C-terminal region of the immunogenic component is encoded by a polynucleotide having the nucleotide sequence of SEQ ID NO. 3.

3. The monocomponent vaccine of claim 1, further comprising one or more polynucleotides that comprise the regions which encode cytokines.

4. The monocomponent vaccine of claim 3, wherein the cytokine is selected from interleukin 12 (IL-12), granulocyte-macrophage colony-stimulating factor (GM-CSF), interleukin 6 (IL-6), interleukin 18 (IL-18), γ-interferon, α,β-interferons and chemokines.

5. The monocomponent vaccine of claim 4, where the cytokine is selected from the IL-12 and GM-CSF cytokines.

6. The monocomponent vaccine defined in claim 1, wherein the immunogenic component is selected from between 10 and 16 repetitive units in the C-terminal region.

7. The monocomponent vaccine defined in claim 1, comprising a recombinant biomolecule formed by the fusion of that region which comprises repetitive units of amino acids and at least one of (i) the polypeptide with trans-sialidase activity, (ii) the polypeptide with cysteine proteinase activity, and (iii) the paraflagellar rod protein (PFR).

8. The monocomponent vaccine defined in claim 1, wherein the immunogen of the immunogenic component is obtained from *Trypanosoma cruzi* trypomastigotes.

9. The monocomponent vaccine defined in claim 1, wherein the immunogen of the immunogenic component is obtained from *Trypanosoma cruzi* amastigotes.

10. The monocomponent vaccine defined in claim 1, which stimulates at least one immune response selected from an antibody response and an immune response by cell mediation.

11. The monocomponent vaccine defined in claim 10, which stimulates at least one response of CD4+Th1 biased T cells and CD8+ T cells.

12. The monocomponent vaccine defined in claim 11, which stimulates at least one response CD8+ T cells.

13. The monocomponent vaccine defined in claim 1, wherein the polypeptide is selected from the TSA-1, ASP-1, ASP-2, hemolysin and Lyt1 proteins.

14. The monocomponent vaccine of claim 1, wherein said vaccine is a therapeutic vaccine.

15. The monocomponent vaccine defined in claim 1, wherein said vaccine is a prophylactic vaccine.

16. The monocomponent vaccine defined in claim 1, wherein the C-terminal region of the immunogenic component is a polypeptide having the amino acid sequence of SEQ ID NO. 4.

17. An isolated polynucleotide encoding one or more polypeptide(s) each having a C-tejininal region composed of at least two repetitive units of amino acids and a eukaryotic promoter operably linked to one or more coding regions for said polypeptide(s), wherein each repetitive unit of amino acids shows the following amino acid sequence:

AHSTPSTPVDSS (SEQ ID NO: 6)

and wherein a polypeptide with trans-sialidase activity of *Trypanosoma cruzi* is fused to the C-terminal region of each of said polypeptide(s), wherein the polypeptide with trans-sialidase activity of *Trypanosoma cruzi* has the amino acid sequence of SEQ ID NO. 2 and is encoded by the nucleotide sequence of SEQ ID NO. 1, and wherein the vaccine further comprises an adjuvant that does not inhibit trans-sialidase enzymatic activity of the immunogen portion, wherein the adjuvant is aluminum oxide.

18. The isolated polynucleotide according to claim 17, wherein the polypeptide with trans-sialidase activity of *Trypanosoma cruzi* has the amino acid sequence of SEQ ID NO. 2 and is encoded by the nucleotide sequence of SEQ ID NO. 1.

19. A plasmid, cosmid or eposome comprising an isolated polynucleotide encoding one or more polypeptide(s) each having a C-terminal region composed of at least two repetitive units of amino acids and a eukaryotic promoter operably linked to one or more coding regions for said polypeptide(s), wherein each repetitive unit of amino acids shows the following amino acid sequence:

AHSTPSTPVDSS (SEQ ID NO: 6)

and wherein a polypeptide with trans-sialidase activity of *Trypanosoma cruzi* is fused to the C-terminal region of each of said polypeptide(s), wherein the polypeptide with trans-sialidase activity of *Trypanosoma cruzi* has the amino acid sequence of SEQ ID NO. 2 and is encoded by the nucleotide sequence of SEQ ID NO. 1, and wherein the vaccine further comprises an adjuvant that does not inhibit trans-sialidase enzymatic activity of the immunogen portion, wherein the adjuvant is aluminum oxide.

\* \* \* \* \*